United States Patent
Rautava

(10) Patent No.: US 6,280,382 B1
(45) Date of Patent: Aug. 28, 2001

(54) COMPENSATION OF CONCENTRATION VALUES CONCERNING A PATIENT

(75) Inventor: Katri Maria Rautava, Espoo (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 09/460,868

(22) Filed: Dec. 14, 1999

(30) Foreign Application Priority Data

Feb. 25, 1999 (EP) .................................................. 99660037

(51) Int. Cl.$^7$ ........................................................ A61B 5/00
(52) U.S. Cl. .......................... 600/364; 73/23.21; 73/23.2
(58) Field of Search ................................... 600/364, 345, 600/483, 484, 529, 532, 533, 538, 300, 309; 73/23.2, 23.21, 23.3

(56) References Cited

U.S. PATENT DOCUMENTS

| | | |
|---|---|---|
| 4,423,739 | 1/1984 | Passaro et al. . |
| 4,585,007 | 4/1986 | Uchigaki et al. . |
| 4,914,719 | 4/1990 | Conlon et al. . |
| 5,186,172 | 2/1993 | Fiddian-Green . |
| 5,479,923 | 1/1996 | Rantala . |
| 6,001,064 | * 12/1999 | Weckstrom .......................... 600/532 |
| 6,112,576 | * 9/2000 | Tsopelas .............................. 73/25.02 |
| 6,147,351 | * 11/2000 | Huiku .................................. 250/343 |

FOREIGN PATENT DOCUMENTS

| | | |
|---|---|---|
| 834733 | 4/1998 | (EP) . |
| 94/21163 | 9/1994 | (WO) . |

OTHER PUBLICATIONS

Dr. Jukka Takala Clinical Application Guide of Gastrointestinal Tonometry, © Instrumentarium Corp., Datex–Ohmeda Division, Finland (894796–1/PG5/0898).

Drs. Guillermo Gutierrez and Steven D. Brown, Gastric Tonometry: A New Monitoring Modality in the Intensive Care Unit, j. Intensive Care Med., 10, pp. 34–44 (1995).

Kirk–Othmer's Encyclopedia of Chemical Technology, Third Edition, vol. 3, Antibiotics (Phenazines) to Bleaching Agents, John Wiley & Sons (New York) pp. 488–490 and 222–223).

Encyclopedia of Polymer Science and Engineering, vol. 9, Liquid Crystalline Polymers to Mining Applications, John Wiley & Sons (New York) pp. 562–563.

Kirk–Othmer's Encyclopedia of Chemical Technology, Matches to N–Nitrosamines, Third Edition, vol. 15, John Wiley (New York), pp. 118.

J.A. Brydson, Polytechnic of North London, Plastics Materials, $4^{th}$ Edition, Butterworth Scientific (London), pp. 93–97.

\* cited by examiner

Primary Examiner—Robert L. Nasser
Assistant Examiner—Navin Natnithithadha
(74) Attorney, Agent, or Firm—Andrus, Sceales, Starke & Sawall, LLP

(57) ABSTRACT

The invention relates to a method for compensating measured concentration values of a first chemical compound (A) within a first internal tract (1*) of a patient, which concentration values ($P_A$) are rendered by a second chemical compound (B), which is becoming present in the body of said patient, to deviate from actual concentration when mixing with the first chemical compound within said first internal tract. Concentration values ($E_B$) of at least said second chemical compound (B) in a second tract (2*) of said patient is measured or derived several times and estimated concentration values ($C_B$) of said second chemical compound is determined simulating its non-detected concentrations in said first internal tract of the patient. The measured initial concentration values ($P_A$) of said first chemical compound (A) in the first internal tract (1*) is corrected by a compensating factor (Fc), whereafter said successive and corrected concentration values ($C_A$) are the respective one for display and/or further use.

22 Claims, 6 Drawing Sheets

COMPENSATION OF CONCENTRATION VALUES CONCERNING A PATIENT

BACKGROUND OF THE INVENTION

This invention relates to a method for compensating measured concentration values of at least a first chemical compound within a first internal tract of a patient, which concentration values as measured are affected by a second chemical compound, which is becoming present in the body of said patient and has a limited transfer speed to mix with the first chemical compound at least in a detection site for said measured concentration values, rendering these measured concentration values to deviate from actual concentration values within said first internal tract. Especially invention relates to a use of the method for compensating measured concentration values of carbon dioxide within an gastrointestinal tract of a patient, which concentration values are affected by at least nitrous oxide, which is being dosed into the respiratory gas of said patient and has a limited absorption and/or diffusion speed to a detection site for said carbon dioxide concentration measurement, rendering its measured concentration values to deviate from actual concentration values.

For example gastric tonometry provides information on the regional partial pressure of carbon dioxide, which relates to the adequacy of perfusion and rate of metabolism of the patient. The tonometric measurement is done in hollow viscus, typically gastrointestinal, by a special catheter, which is inserted nasogastricly into the stomach or gut. The catheter tip includes a gas-permeable and liquid-impermeable balloon. Carbon dioxide present or developing freely equilibrates between the gastric mucosa, the gastric lumen, and the gas contents of the balloon. After an equilibrium time the catheter gas content corresponds to the gas or liquid composition in the gastric mucosa. Gastric tonometric monitoring apparatus may be designed to automatically infuse and sample gas mixture from the catheter balloon at intervals and then automatically provide data of the carbon dioxide ($CO_2$) concentration of the gas sample e.g. with the infrared absorption technique. Gastric tonometry is currently used mainly for intensive care patients, but it is increasingly used also for surgical patients during longer operations.

The hepatosplanchic area, which is the usual site of tonometric measurement, has an important role in the pathogenesis of the multiple organ dysfunction syndrome. Splanchnic tissue perfusion has a low priority in the acute circulatory failure. Blood circulation is redistributed during a hypovolemic or cardiogenic shock so, that the most vital organs, heart and brain, get enough blood. Even though the reduction of splachnic tissue perfusion may initially be vital for survival, the prolonged reduction of splanchnic blood increases the risk of tissue damage and organ dysfunction and failures and even death of the patient. The medical background of this phenomenon is disclosed in a booklet published by the applicant: Jukka Takala—"Clinical Application Guide of Gastrointestinal Tonometry", © Instrumentarium Corp., Datex-Ohmeda Division, Finland (894796-1/PG5/0898) and Guillermo Gutierrez, Steven D. Brown, "Gastric Tonometry: A new Monitoring Modality in the Intensive Care Unit", J Intensive Care Med, 10, pages 34–44, 1995. The inadequate tissue perfusion and/or increased metabolic rate can be seen as an increased partial pressure of carbon dioxide ($P_{CO2}$) in the tissue. During inadequate perfusion tissue is not oxygenated well enough, which leads to the anaerobic metabolism and thus increased production of carbon dioxide. Carbon dioxide level in the tissue is also increasing, because it cannot be removed effectively from the tissue. If the increased $P_{CO2}$ level can be detected early enough, the patient can be recuscitated better. This problem is discussed in the publication WO-94/21163 and a method is suggested, according to which the partial pressure of carbon dioxide is measured in hollow viscus and the carbon dioxide level or the pH of arterial blood is measured as well, and a parameter, more detailed called either a $pCO_2$-gap or a pH-gap, indicative of condition of the hollow viscus is determined on the basis of these two values. The carbon dioxide level of the arterial blood might also be measured through detection of the end tidal partial pressure ($pCO_2$) of carbon dioxide to describe the overall "global" or "systemic" bicarbonate content of the blood. The pH-gap is calculated by mathematically subtracting intramucosal pH from arterial pH, but calculating $pCO_2$-gap is not clearly described. The additional detection and independent display of anaesthetic gases, such as $N_2O$, in the aspirated air of the patient using separate techniques is mentioned, which is very elaborate method and requires additional equipment.

The partial pressure ($P_{CO2}$) of carbon dioxide level in the gastrointestinal area is determined by analysing the carbon dioxide ($CO_2$) concentration sampled from the tonometric catheter balloon. The measurement/detection technique for determining this partial pressure ($P_{CO2}$) of carbon dioxide is utilises an infrared absorption sensor. An infrared sensor typically comprises an infrared radiation source, gas measuring chamber, at least one optical bandpass filter within an absorption peak of $CO_2$ and an infrared detector delivering an electrical signal proportional to the amount of carbon dioxide in the measuring chamber. The purpose of the optical bandpass filter, like interference filter, is to choose the wavelengths, where $CO_2$ molecules absorb infrared (IR) light. This kind of measuring sensors and measuring apparatuses are widely known and are generally available in the market by several manufacturers and used for many different measuring purposes. So it is not necessary to describe them more detailed. Nitrous oxide ($N_2O$) is commonly given to surgical patients in very high concentrations (20–80%) as an anaesthetic gas in the respiratory tract. A typical inhaled gas mixture includes in the order of 60–70 vol.-% of $N_2O$ and in the order of 25–30 vol.-% oxygen, and further containing an additional vaporised anaesthetic agent as halothane, desflurane, isoflurane, enflurane and/or sevoflurane usually less than about 12 vol.-%. There is known a special measurement error caused by $N_2O$ to $CO_2$ because of spectral line broadening, also called collision broadening. This error depends on the $CO_2$ sensor, but typically this error can be about +10% (relative) with 70 vol.-% $N_2O$ concentration. So if the true gas mixture contains 10 vol.-% $CO_2$ and 70% of $N_2O$ and balanced nitrogen ($N_2$), an uncorrected infrared absorption sensor described above shows a value 11 vol.-% carbon dioxide. This error is normally not acceptable in tonometric measurement and should be somehow corrected. This problem is typical when measuring with an optical bandpass filter having a narrow transmission band, which extends across several rotational lines of an absorption peak. In this case a detector "sees" an increased absorption value, due to the fact that this kind of measuring arrangement detects transmission instead of actual absorbance. Especially polar gases, $N_2O$ being one of them, have a major effect on spectral line broadening. It is also possible that e.g. intravenous dosage of drugs or medicinal preparations or additives into the patient may affect the concentration measurements of a chemical compound in an internal tract or organ, either because of spectral line broadening or an overlapping absorption described later.

One way of compensating the line broadening error caused by $N_2O$ is to use a double detector combination as a sensor arrangement, which detectors simultaneously measure both the $CO_2$ and the $N_2O$ concentrations in the same gas mixture. This measurement can be done by positioning two optical filters, which have different radiation transmitting bands, one for $CO_2$ and one for $N_2O$, to detect IR-radiation absorption in a measuring chamber. When both concentrations in the same gas mixture are thus known, a linear mathematical correction model can be applied to $CO_2$ concentration. This kind of sensor arrangement and correction method is disclosed in publication U.S. Pat. No. 4,423,739 to correct the carbon dioxide measurement result of exhaled air using the nitrous oxide measurement result of the same exhaled air. Both measurements are performed simultaneously at the end tidal of the patient's exhaled breath. The publication teaches a formula for said correction of $CO_2$ in presence of $N_2O$ as follows:

$$(C_{CO2})_{breath} = (E_{CO2})_{breath}[1 + K \cdot (E_{N2O})_{breath}] \quad (1),$$

where $C_{CO2}$=corrected $CO_2$ concentration in exhaled air, $E_{CO2}$=measured $CO_2$ concentration in exhaled air, $E_{N2O}$=measured $N_2O$ concentration in exhaled air, and K is an empirical spectral line broadening constant. This disclosed method and apparatus have several drawbacks. For example each gas component, which might be present and might contribute to collision broadening must be measured separately, which is unpractical, because at least individual optical bandpass filter(s) and measuring channels are required for each gas component rendering the large and too heavy sensor, and unreliable, because the gas mixture may include varying amounts of hard-to-measure gas components.

Another publication EP-0 834 733 discloses a totally different method for correcting the spectral line broadening error, with utilising a measured viscosity or viscosity related quantity of the gas mixture. This method also requires an use of additional detection means, and hence are impractical in many cases, where a small and light-weight detector arrangement is needed or is preferable.

An additional problem, independent of said spectral line broadening, is the generally known overlapping absorption of different gas components in a gas mixture, which means that these gas components have absorption peaks very close to each other, whereupon it is difficult to separate the transmissions or absorptions thereof, because each signal from detectors provided with different optical bandpass filters—and intended for a specific gas component—includes transmission/absorption data from at least one other gas component. One suggestion for solving this problem is disclosed e.g. in publication U.S. Pat. No. 4,914,719, according to which the same amount of signals, each gained by an optical bandpass filter with a center wavelength different from the center wavelengths of the other filter, is required, and the center wave-lengths and the passband widths are chosen to represent the concentrations, and algebraically combining the determined concentrations of each gas component. This might be a working method, but has the same drawbacks and problems as mentioned above in the context of U.S. Pat. No. 4,423,739.

BRIEF SUMMARY OF THE INVENTION

Thus, the main object of this invention is to find a method for correcting a by detection measured concentration value of a first gas component, which measured concentration value is affected by a second gas component in the gas mixture, without several detectors for separate measuring of each of said at least two gas components. This means, that the detector arrangement for measuring the first gas component should be kept small, lightweight and simple. The second object of this invention is to find a method, which provides applicability to measure the first gas component in any necessary body part of a patient, which means that the method should not as such restrict the site for detection. The site of detection, from which the gas mixture to be analysed is gathered, and is then transferred, if necessary, to a measuring chamber of the measuring apparatus, should be selectable on medical or other practical basis not essentially limited by the method. The third object of this invention is to find a method, which provides data and/or calculations for correction of concentration value of the first gas component with acceptable accuracy. The fourth object of this invention is to find a method, which is also applicable under conditions, where the second gas component is transferred or dosed into the body of the patient in an area or organ(s) separate from said detection site for the first gas component, and/or applicable under conditions, where the second gas component has a limited transfer speed to said detection site for the first gas component. If only possible the method should allow the first gas component to occur mixed with another medium, like liquid or solid or tissue in that body section of the patient, where the site for detection is decided to be. A further limited object of the invention is to find this kind of method, which could be applied in the field related to medical diagnostics and/or intensive care and/or other medical or clinical operations.

The problems and drawbacks described above can be eliminated and the defined objects are achieved by means of the inventive method according to and by means of the inventive use according to the claims.

Now it has been surprisingly found that by utilising concentration values of a second chemical compound from a second tract of a patient, which chemical compound affects the measured concentration value of a first chemical compound detected by a radiation absorption in a first internal tract of said patient, it is possible to correct the initial concentration value of the first chemical compound. This is a very practical procedure especially in cases, when the concentration of the second chemical compound from a second tract of the patient is possible to receive from other existing equipment connected to the patient, but can be favourable also in cases when an additional detector arrangement or output from a dosing apparatus is needed. In every case there no need for extra detectors in that measuring apparatus, which is used for detecting and outputting or displaying the concentration of the first chemical compound in the first internal tract of said patient, whereupon the small size and weight of the detector arrangement can be maintained. It has also been surprisingly found that accurate enough correction of the initial measured concentration value of the first chemical compound in the first internal tract can be achieved using the further features of this invention.

BRIEF DESCRIPTION OF THE SEVERAL VIEWS OF THE DRAWING

The invention is now described in detail with reference made to the accompanying figures.

DETAILED DESCRIPTION OF THE INVENTION

Figure 1:
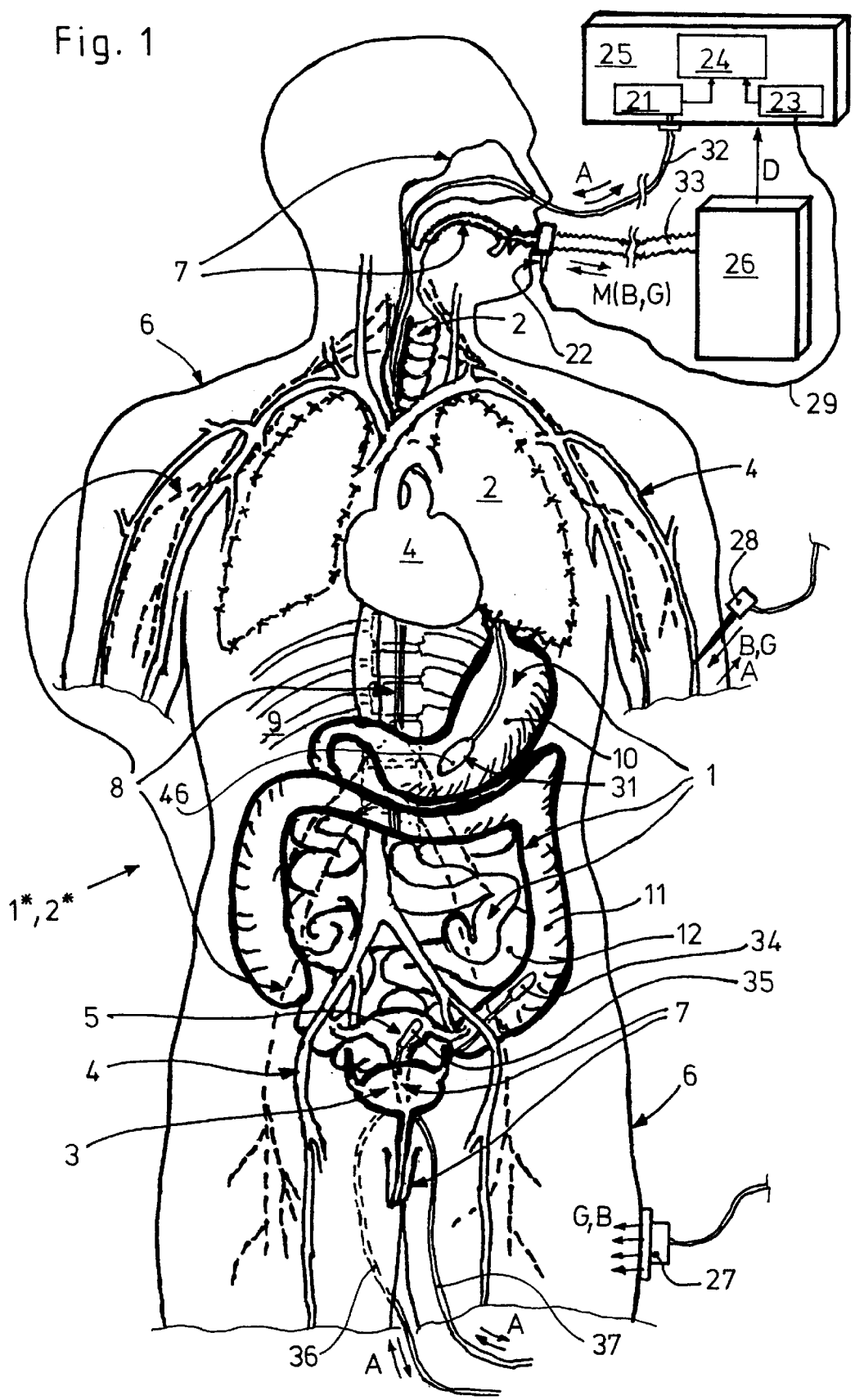
FIG. 1 shows generally and schematically a body of a human and some of his/her internal and external tracts, which include the optional detection sites of the invention. Detection site is a point in the patient, wherefrom the required concentration values shall originate. Some of the possible detector arrangements are shown guided in their operation position. This figure also shows schematically one possible embodiment for a measuring apparatus with a first detector arrangement for measuring concentration of a first chemical compound within a first internal tract of a patient and a second arrangement for measuring or deriving concentration of a second chemical compound within a second tract of a patient. Advantageously e.g. for clinical purposes $CO_2$ concentration value is measured with an gastrointestinal tonometry and at least $N_2O$ concentration value is from the respiratory gas/air.

According to one advantageous embodiment of the invention the measured or derived nitrous oxide concentration from a respiratory tract 2 of a patient is used for correcting an error of measured carbon dioxide concentration in gastrointestinal tract 1. To detect the carbon dioxide concentration a catheter with a tonometric balloon 31, which is gas-permeable, but liquid-impermeable, is guided nasogastrically into the gastric hollow organs, usually within stomach 10, or possibly within colon 11 or small intestine 12. The gaseous content of the balloon 31 is then analysed using infrared absorption technique as described earlier in this text. Especially for clinical operations, like surgery and intensive care, the measured concentration values of carbon dioxide $CO_2$ within an gastrointestinal tract 1 of a patient are compensated using the inventive method to get an accurate value thereof. The initial $CO_2$ concentration values detected from the gastrointestinal tract 1 are affected by at least nitrous oxide $N_2O$, which is generally being dosed in the respiratory gas M of the patient as an anaesthetic medium. The $N_2O$ dosed and inhaled has a limited or low absorption and/or diffusion and/or transport speed from the pulmonary area through tissue to the gastric mucosa, but has a much higher diffusion speed to the catheter balloon than $CO_2$. Both $N_2O$ and $CO_2$ has a limited absorption speed through the wall 45 of catheter balloon 31. After a catheter equilibrium time, the $N_2O$ partial pressure in gastric area should be close to the partial pressure $P_{N2O}$ in the tonometric balloon.

So in this practical case the intestinal hollow organ like stomach 10 is the point of interest and so the detection site, wherefrom necessary predefined data shall be available, in order that the medical state of the patient can be evaluated. As already described accurate gastrointestinal $CO_2$ concentration is one required data for evaluation of hepatosplanchic area 9. The measurement or detection of $CO_2$ concentration can be performed in detection site or any other position, as described later, but the valid gas mixture, which is analysed, shall be gathered from said detection site, that is in the point of interest, with the aid of e.g. tonometric balloon. As mentioned earlier at least the nitrous oxide present in the intestinal tract and so in the gas mixture within the tonometric balloon causes the measured carbon dioxide concentration values $P_{CO2}$ to deviate from actual concentration values. According to the invention concentration values $E_{N2O}$ of at least nitrous oxide is measured or derived several times in the inhaled or exhaled gas M of said patient, that is in the respiratory tract 2, during a period T of a clinical operation. Further the concentration values $C_{N2O}$ for nitrous oxide within the gastrointestinal tract are estimated without detection therein and the measured initial concentration values $P_{CO2}[n]$ of carbon dioxide in the gastrointestinal tract 1 are corrected by a compensating factor Fc.

The basic features of the invention is a determining of e.g. $N_2O$ using a new method. The applied basic formulas in the special case described above are as follows:

$$\{C_{CO2}\}_{gastric} = P_{CO2}[1+Fc] \qquad (I_S)$$

and $$Fc = K \cdot (C_{N2O})_{respiratory} \qquad (II_S)$$

where $C_{CO2}$=corrected $CO_2$ concentration in gastrointestinal tract 1, $P_{CO2}$=measured $CO_2$ concentration in gastrointestinal tract 1, $C_{N2O}$=estimated $N_2O$ concentration value calculated from measured or derived $N_2O$ concentration or concentrations in respiratory tract 2 (=exhaled or inhaled air), and K is an empirical spectral line broadening constant. Fc is a compensating factor described later. This above described method is utilised e.g. during surgical operations or intensive care to detect the rate of metabolism and/or perfusion in the patient. It is clear that these functions can be written in a general form as:

$$\{C_A\}_{(1)} = P_A \cdot [1+Fc] \qquad (I_B),$$

and $$Fc = K \cdot (C_B)_{(2)}, \qquad (II_B),$$

where A means any measurable first chemical component, as any gas in a gas mixture, which chemical component is to be measured by detection in a first internal tract 1\* or organ of a patient, the concentration of which shall be available to personnel, like research or clinical workers. Here B means a second chemical component mixing with the first chemical component and causing an error to the measured initial concentration values $P_A$ so that it deviates from the actual concentration value $PR_A$. The second chemical component is measured in a sample taken from a second tract 2\*, which can be an internal tract or an external area of the patient. The lower indices $_{(1)}$ and $_{(2)}$ in the formulas $I_B$ and $II_B$ refer to the first and second tract respectively. In general the first internal tract 1\* can be an intestinal tract 1, or a respiratory tract 2, or an urinary tract 3, or one of the vascular tracts 4, or a genital tract 5, and the second tract 2\* can be an intestinal 1 tract, or a respiratory tract 2, or an urinary tract 3, or a nervous tract 8, or one of the vascular tracts 4, or a genital tract 5, other than the first internal tract, or a cutaneous or mucous area 6, 7 of the body of the person or animal. Preferably said first chemical compound A is arranged to be in the gaseous state using tonometric means 31, 34, 35 within said first internal tract 1\*, whereupon this first tract can be either the intestinal tract 1, or the urinary tract 3, or the genital tract 5 or any other accessible internal hollow organ of the patient or a person or an animal. Alternatively the second chemical compound B and the first chemical compound A is arranged to be in the gaseous state using air or gas mixture, like breathing air M, provided to or from said second internal tract 2\* with a dosing apparatus 26, whereupon this second tract can be either the intestinal 1 tract, or the respiratory tract 2 or any other accessible hollow organ. The second chemical compound B may also be in a liquid state when provided to said second internal tract 2\*, whereupon this second tract can be either the intestinal 1 tract, or the urinary tract 3, or the nervous tract 8, or one of the vascular tracts 4, or the genital tract 5, or a cutaneous or mucous area 6, 7 of the body of a patient or a person or an animal. In liquid state the second chemical compound B can be dosed either in a hollow organ, or transcutaneously with an pressure unit 27 or through injection unit 28 into other internal organs. It is also possible to draw the first chemical compound A as a part of a liquid, like blood, using injection unit 28 in reverse mode. According to the invention the second internal tract 2\* is other portion of a body than the first internal tract 1\*. The second chemical compound B and/or the third chemical compound G described below can be directly dosed in a controlled manner into the patient, or one or both of them can be basically end up in the patient or person or animal because of an uncontrolled reason, but in every case that amount of these chemical compounds, which is received by said body, shall be measurable. So at least the concentration values $C_{N2O}$ for nitrous oxide are measured or derived, by detection or by using, dosing data D directly from a dosing apparatus 26, from that area or channel forming a dosing route of the nitrous oxide $N_2O$ into the patient.

If there are e.g. two error causing chemical components, the above mentioned component B and an additional chemical component G, the formulas ($I_B$) and ($II_B$) is written in an altered form:

$$\{C_{AG}\}_{(1)} = P_A \cdot [1+Fc] \cdot [1+Fc^*] \qquad (I_{BG}),$$

where $$Fc = K_B \cdot (C_B)_{(2)}, \qquad (II_B),$$

and $$Fc^* = K_G \cdot (C_G)_{(2)}, \qquad (II_G).$$

Where $K_B$ and $K_G$ are empirical spectral line broadening constants, and Fc is a first compensating factor and Fc\* is a second compensating factor described later. This is practical when there are one or several of those other anaesthetic gases, which is/are being dosed into the respiratory air of said patient, and the concentration values $E_G$ of at least one of them, is/are additionally measured in the second tract 2\* or derived as a data D from a dosing apparatus 26 as later described in more detail. In these cases also the concentration values $C_G$ for specified anaesthetic gas component(s) within gastrointestinal tract 1 are estimated without detection according to the invention, and an altered additional compensating factor Fc\* is formulated to provide a further correction for measured initial concentration values $P_{CO2}[n]$ of carbon dioxide or generally concentration value $P_A[n]$ of gas component. Further the third or several chemical compound(s) G, which is/are received by said body and further transferred to the detection site can be measured or derived in an third area or tract 3\* deviating at least from the first internal tract and possibly from the second tract 2\*. Concentration value(s) $C_G$ thereof is/are estimated without detection as described later.

According to the invention the actual $PR_{N2O}$ in gastrointestinal tract 1 is simulated by estimating a value $C_{N2O}$ therefor using a recursive exponential smoothing having a mathematical equation:

$$Y(t) = (1-\gamma)^{t+1} X(0) + \sum_{u=0}^{t} \gamma (1-\gamma)^{t-u} X(u) \qquad (2)$$

where X=input value, Y=output value, γ=smoothing parameter, and a recursive form for exponential smoothing formula in general form:

$$Y(t+1) = \gamma \cdot X(t+1) + (1-\gamma) \cdot Y(t) \qquad (3)$$

When this equation is applied to specific clinical conditions, like surgery or other clinical operation like intensive care of a patient, and so for nitrous oxide $N_2O$ and for determining the estimated concentration value $C_{N2O}$ within e.g. gastrointestinal tract 1 using its by detection measured or by other means derived concentration value $E_{N2O}$ within e.g. respiratory tracts 2, the equation reads as follows:

$$C_{N2O}[n]=\gamma(n)\cdot[E_{N2O}(n)]+[1-\gamma(n)]\cdot[C_{N2O}(n-1)] \quad (III_S),$$

where (n) is the number of measurements and so (n−1) the number of the previous measurement. Typically the time between two tonometric measurements is 10 minutes and over a time period T including first traces of $N_2O$ or said second chemical compound B respectively within or in contact with said patient, and especially from the beginning of dosage of nitrous oxide $N_2O$ into a patient under said clinical operation. The inventive estimated concentration value $C_{N2O}$ is so a predetermined cumulative function of a prevailing concentration value $E_{N2O}$ e.g. in the respiratory tract 2 and previous estimated concentration values $C_{N2O}$ [n−1] in the gastrointestinal tract 1. This estimated concentration value $C_{N2O}$[n] is used in conjunction with formula $II_S$ to get the compensating factor Fc.

According to one embodiment of the invention the smoothing parameter $\gamma(n)$ is dependent on perfusion related parameters, in this case the measured partial pressure $P_{CO2}$ of carbon dioxide in the gastric organ 10 and the measured partial pressure $E_{CO2}$ in the end tidal of inhaled or exhaled air, and more detailed form the $P_{CO2}$(n−1) and $E_{CO2}$(n−1). In this case additionally a concentration value $E_{CO2}$ of carbon dioxide is measured or derived several times in the inhaled or exhaled gas M of said patient during a period T of the clinical operation. Then the following formula can be used:

$$\gamma(n)=\eta/[(P_{CO2}(n-1)-E_{CO2}(n-1)+\sigma] \quad (IV_{aS}).$$

Alternatively according to another embodiment of the invention the smoothing parameter $\gamma(n)$ is dependent on the estimated value $C_{CO2}$(n−1) of carbon dioxide in the gastric organ 10 and the measured partial pressure $E_{CO2}$ in the end tidal of inhaled or exhaled air and $E_{CO2}$(n−1), whereupon:

$$\gamma(n)=\eta/[(C_{CO2}(n-1)-E_{CO2}(n-1)+\sigma] \quad (IVb_S).$$

Alternatively according to a further embodiment of the invention the smoothing parameter $\gamma(n)$ is dependent on the estimated value $C_{CO2}$(n−1) of carbon dioxide in the gastric organ and on the arterial concentration of $CO_2$ (=$R_{CO2}$), whereupon:

$$\gamma(n)=\eta/[(C_{CO2}(n-1)-R_{CO2}(n-1)+\sigma], \quad (IVc_S),$$

and
alternatively according to further embodiments of the invention the smoothing parameter $\gamma(n)$ is dependent on the $P_{CO2}$(n−1) only, or non-dependent from any concentration value having a constant value. For instance:

$$\gamma(n)=\eta/[(P_{CO2}(n-1)+\sigma] \quad (IVd_S),$$

respectively $$\gamma(n)=\text{constant} \quad (IVe_S).$$

Initial value $C_{N2O}$(0), that is the calculated value of $N_2O$ at the beginning (n=0) of measurement time period T has to be known. Before the beginning of a surgical operation $C_{N2O}$(0) is evidently zero. This can be verified by looking the $E_{N2O}$, which should be also zero in that case. In all of the formulas the concentration marking C means a corrected or estimated concentration value, marking P means a measured value from any first tract, marking E means a measured or derived—e.g. data D transferred from dosing apparatus 26 to display unit 24—value from any second tract, and marking R means a measured or derived value from a further tract of the patient obtained by detection or data transmitting.

The equation disclosed above can be readily amended to be aimed at a general case, like equations ($I_G$) and ($II_G$) and would read as follows:

$$C_B[n]=\gamma(n)\cdot[E_B(n)]+[1-\gamma(n)]\cdot[C_B(n-1)] \quad (III_S),$$

whereupon the estimated concentration value $C_B$[n] so is a cumulative function of one in succession previous estimated concentration value $C_B$[n−1], and is directly related to both a measured or derived concentration value $E_B$[n] and a previous estimated concentration value $C_B$[n−1] thereof, and is additionally related to a constant stant or variable parameter γ. This estimated concentration value $C_B$[n] is used in conjunction with formula $II_B$ to get the compensating factor Fc, and an analogous estimated concentration value $C_G$[n] similarly in conjunction with formula $II_G$ to get the compensating factor Fc*. The formulas for the smoothing parameter $\gamma(n)$ can be anagolously as follows:

$$\gamma(n)=\eta/[(P_A(n-1)-E_A(n-1)+\sigma] \quad (IVa_G),$$

$$\gamma(n)=\eta/[(C_A(n-1)-E_A(n-1)+\sigma] \quad (IVb_G),$$

$$\gamma(n)=\eta/[(C_A(n-1)-R_A(n-1)+\sigma] \quad (IVc_G),$$

$$\gamma(n)=\eta/[(P_A(n-1)+\sigma] \quad (IVd_G),$$

and $$\gamma(n)=\text{constant} \quad (IVe_G).$$

So the smoothing parameter γ has at least successive actual concentration values of the first chemical compound A from said first and/or second tract 1* and/or 2* as variables. The estimated concentration value C is an inverse function of these actual concentration values P, E, R of at least one of the chemical compounds in one of tracts. The advantage of the currently introduced method is the calculation convenience. It needs the history data only one step backward, if tonometric measurement is started before giving $N_2O$ to the patient, though the method is genuinely cumulative. If tonometric measurement is started in the middle of the operation—that is later than from the beginning of dosing anaesthetics B, or $N_{O2}$, or halothane etc., or later than the moment of first traces of contact thereof—then the approximation for the current $N_2O$ concentration in the stomach or any other first internal tract 1* can be calculated recursively from the formula (2), if $N_2O$ trend data is available. The same formulas apply to any error causing gas component whether a second or a third or a fourth etc. chemical compound. The formula or equation for simulation of the estimated concentration value $C_{N2O}$, or generally $C_B$, is selected or formulated empirically. So it is possible to use one of the formulas III and IVa to IVb or it is possible to formulate a new different formula or equation on the basis of empirical data from patients. Accordingly the invention is not limited to these formulas disclosed.

The dependence of smoothing parameter $\gamma(n)$ on $P_{CO2}$(n) and $E_{CO2}$(n) needs some checks: If $P_{CO2}$ is smaller that $E_{CO2}$, the $P_{CO2}$ value is probably not correct and then shouldn't be used in the calculation. This is the case for instance with two first tonometric measurements, which are not yet correct. In this case it is suggested to use a constant ($P_{CO2}$−$E_{CO2}$) value, for instance 0.5 Kpa.

Figure 2A:
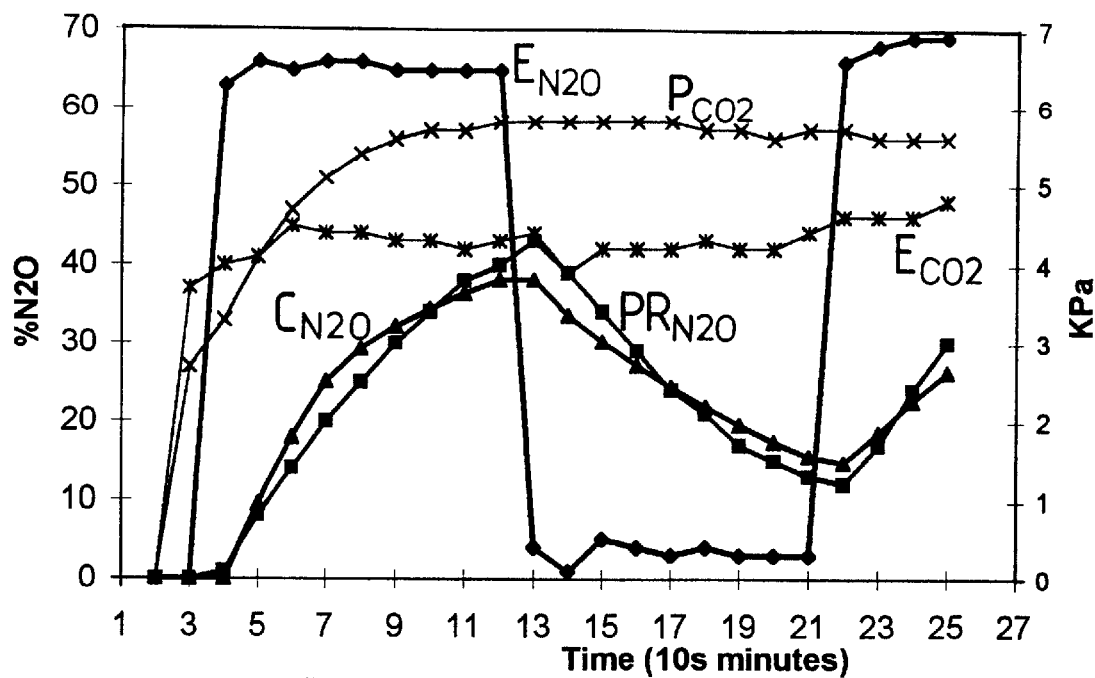
FIG. 2A illustrates a first example of the relationship between a gastrointestinally measured $CO_2$ concentration, a $N_2O$ and $CO_2$ concentrations measured from exhaled air, and estimated $N_2O$ concentration defined according to the invention and time during a surgical operation of a patient. For comparison purposes is a gastrointestinally measured $N_2O$ concentration also shown, which concentration is not measured in practise.
Figure 2B:
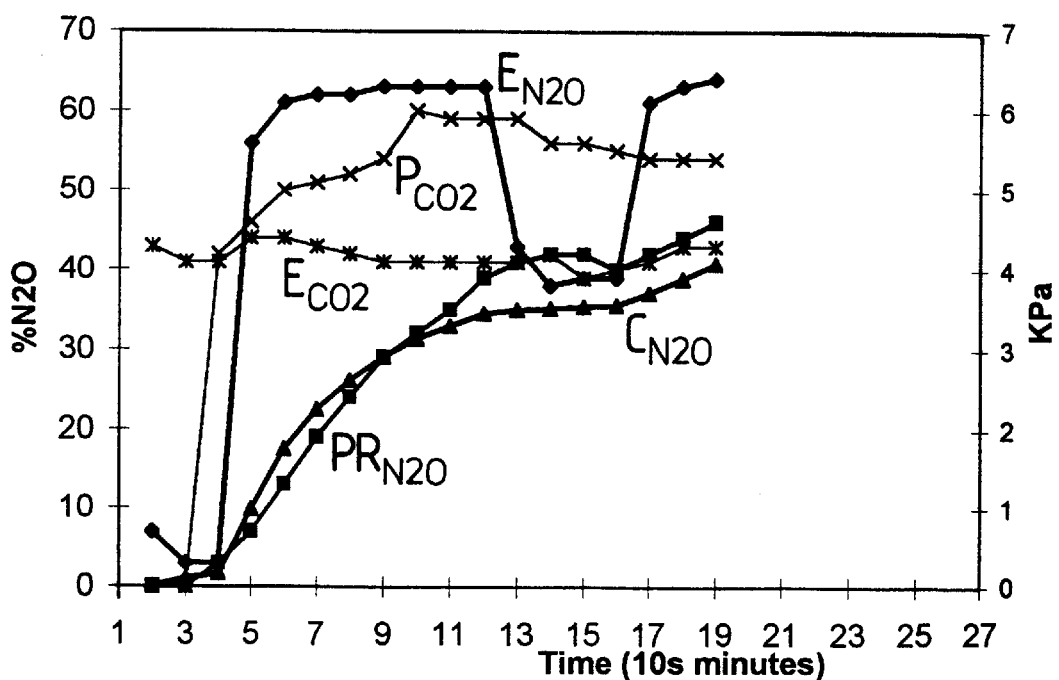
FIG. 2B illustrates a second example of the relationship between a gastrointestinally measured $CO_2$ concentration, a $N_2O$ and $CO_2$ concentrations measured from inhaled air, and estimated $N_2O$ concentration defined according to the invention and time during a surgical operation of another patient. For comparison purposes is a gastrointestinally measured $N_2O$ concentration also shown, which concentration is not measured in practise.
Figure 2C:
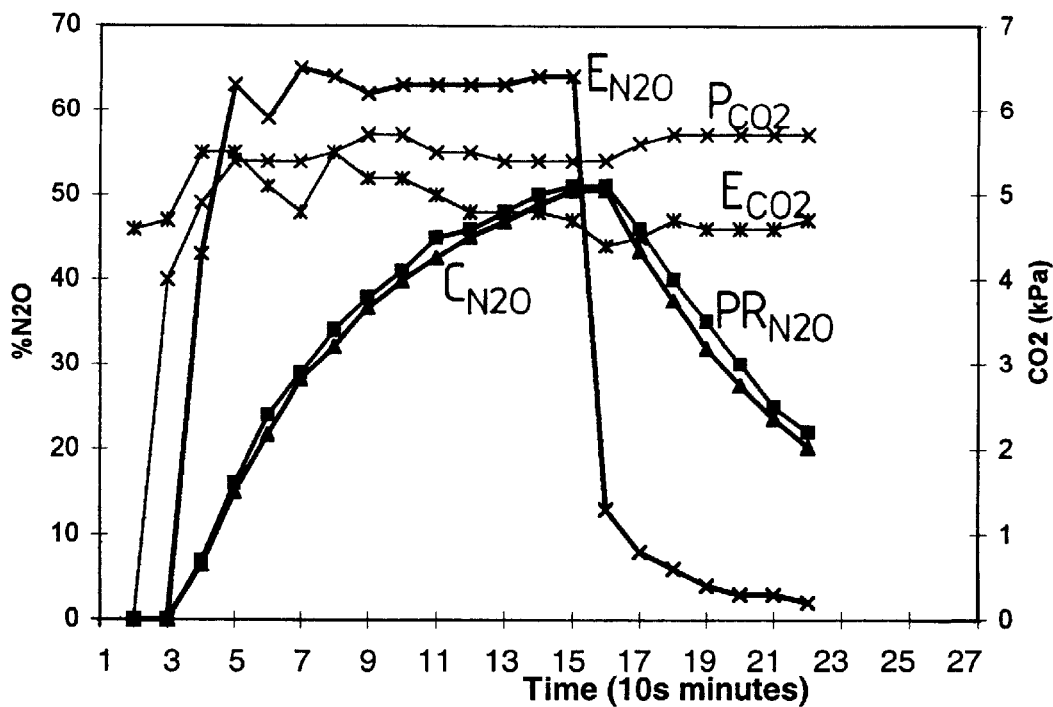
FIG. 2C illustrates a third example of the relationship between a gastrointestinally measured $CO_2$ concentration, a $N_2O$ concentration derived from dosing apparatus and $CO_2$ concentration measured from respiratory air, and estimated $N_2O$ concentration defined according to the invention and time during a surgical operation of a patient. For comparison purposes is a gastrointestinally measured $N_2O$ concentration also shown, which concentration is not measured in practise.
Figure 3:
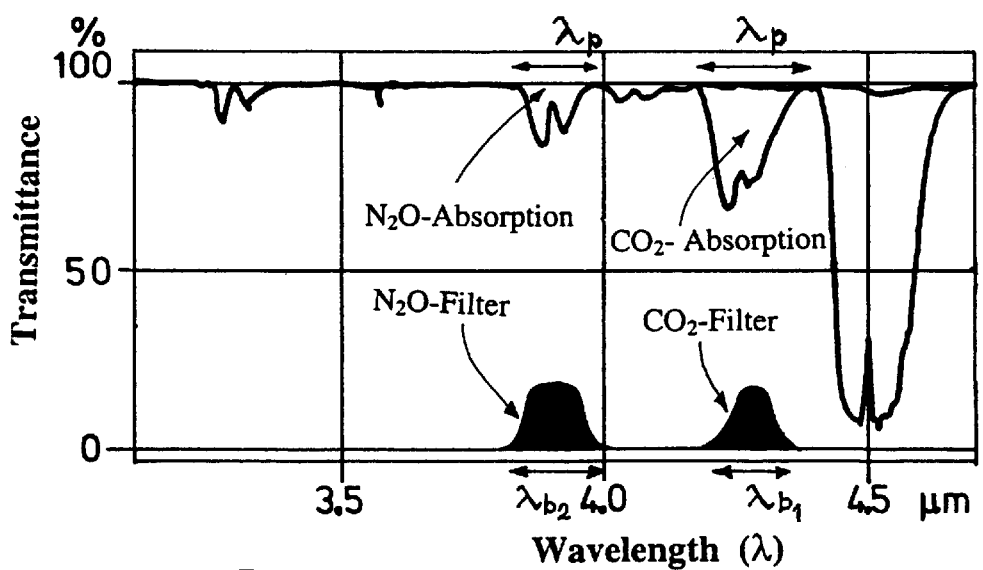
FIG. 3 shows the approximate absorption peaks of e.g. carbon dioxide at a wave length area of 4.3 $\mu$m and nitrous oxide at a wavelength area of 3.9 $\mu$m, and the absorption spectra of the respective optical IR passband filters.
Figure 4:
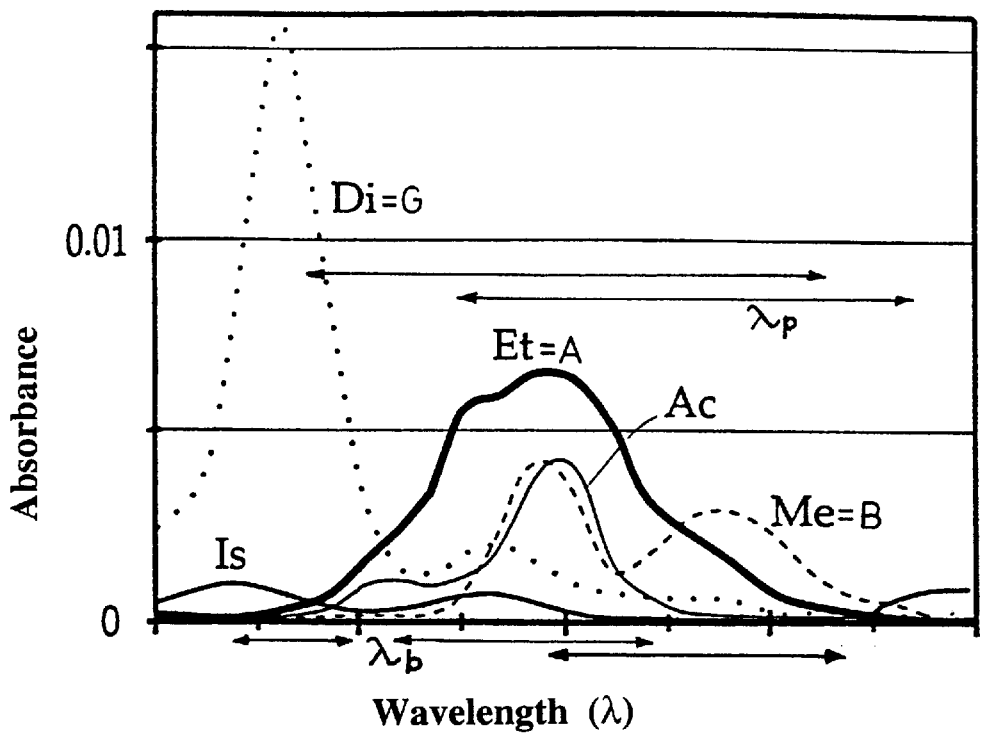
FIG. 4 shows the absorption curves of some chemical compounds Di, Is, Et, Ac and Me being in gaseous state and having overlapping absorption bands in another portion of IR.
Figure 5:
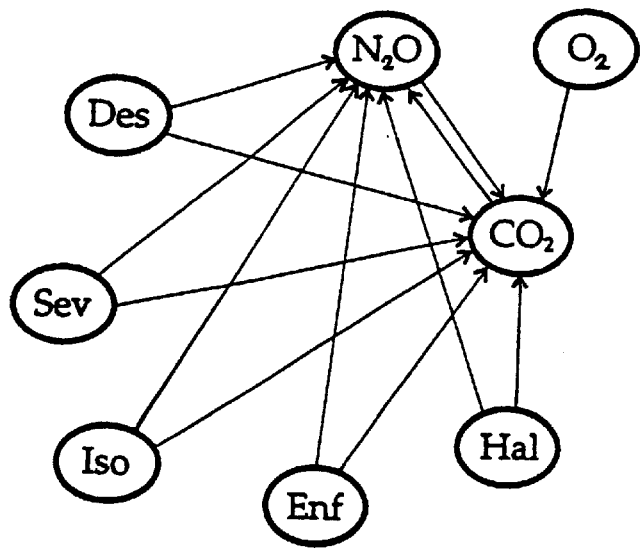
FIG. 5 shows schematically the spectral line broadening interactions between the main gas components of a gas mixture for respiratory air used for anaesthetic purposes during e.g. a surgical operation.

This method is validated for 14 surgical patients and the maximum estimation error for $P_{N2O}$ was approx. 15 vol. %, which is acceptable, if $C_{N2O}$ is used for compensation purposes. In most cases the estimation error was between 5% and 10%. Different test cases are shown in FIGS. 2A to 2C. In the case of FIG. 2A the dosage of nitrous oxide is replaced by other anaesthetic gases in the middle of the operation. In spite of this disturbance the method according to invention results very accurate estimated concentration $C_{N2O}$ of nitrous oxide in the gastric area as compared to measured actual concentration $PR_{N2O}$ of nitrous oxide in that area. The similar accurate results are also found in cases of FIGS. 2A and 2B, where the estimated concentration $C_{N2O}$ of nitrous oxide in the gastric area follows very strictly the measured actual concentration $PR_{N2O}$ of nitrous oxide. Of course the concentration $PR_{N2O}$ or any respective one is not measured/detected in the first tract 1* in practise, here there are specially measured for test purposes only. According to currently made clinical measurements the gastrointestinal $CO_2$ concentration $P_{CO2}$ is not equivalent to end tidal $N_2O$ concentration $E_{N2O}$ from inhaled or exhaled air of a patient, but it is close to a strongly low pass filtered $E_{N2O}[n]$. It can also seen that if the patient is badly perfused in the gastrointestinal area with a high $P_{CO2}$ compared to $E_{CO2}$, the convection of $N_2O$ on the that area is slower. This inventive estimation method is also applicable for other non-metabolic gases e.g. anaesthetic gases.

The method according to invention is also applicable to cases, where it is at least two gas components having overlapping absorption spectra in the gas mixture to be analysed in the first internal tract 1*, and one of the components is the critical one to be accurately measured [=first chemical compound A] and at least another of the gas components [=second chemical compound B] is becoming present in the body of the patient, person or animal e.g. from another source [=second tract 2*], so that it can be measured in some point of the route it originates. After measuring or deriving the concentration data of said second chemical compound B within said second tract 2* its concentration is simulated by the inventive method, and the concentration of chemical compound A within said first internal tract 1* can be corrected very much like above:

$$\{C_A\}_{(1)} = Q1 \cdot \{P_A\}_{(1)} - Q2 \cdot \{C_B\}_{(2)} \quad (I_L),$$

and in case there are two error causing gas components present, the formula widens as follows:

$$\{C_{AG}\}_{(1)} = Q1 \cdot \{P_A\}_{(1)} - Q2 \cdot \{C_B\}_{(2)} - Q3 \cdot \{C_G\}_{(2)} \quad (I_{LG}),$$

where markings are as defined earlier in this text, and compensating factors Q1, Q2 and Q3, in general form Qx, are preferably empirical overlapping constants or variables, which are proportional to the ratio of absorptivities of the chemical compounds in question. The initial measured concentration $P_A$, which is at least partly corrected by a factor Q1, is preferably further corrected—typically by subtraction—by additional terms, which are functions of compensating factors Q2 and Q3 and respective estimated concentration values $C_B$ and $C_G$. These values $C_B$, $C_G$ and possible further concentrations are calculated cumulatively in the same inventive way as described by e.g. referring to formulas 2 to 3 as well as III and IVa to IVe earlier in this text, providing an estimated concentration value to simulate their actual concentration without their detection in the first tract 1*. In order to get factors Qx to be essentially constants a prerequisite for this method in the occasion of overlapping is that the error caused by a gas component is or can be altered to be approximately linearly related to its concentration, which can be done for example by a proper selection of passband widths and peak transmittances of the optical filters used. In this case also the third chemical compound G can be transferred to the body trough the same or different route than the second chemical compound B. As earlier described the second and/or third chemical compounds are allowed to have and variable concentration in its area or tract, where the compound is received from to said body with time, but the concentration data in this second tract 2* shall be available. Mixing with said first chemical compound in the first internal tract 1* is also happening with a time lag, because of limited absorption or diffusion or transport speed in the body tissue and along tracts, like vascular system. A limited absorption or diffusion or transport speed is always present, because it can only be avoided when the second or third chemical compound is received by the body as a ready mixture, and the detection site—site of interest—is the same tract than the tract used for dosage.

Figure 8:
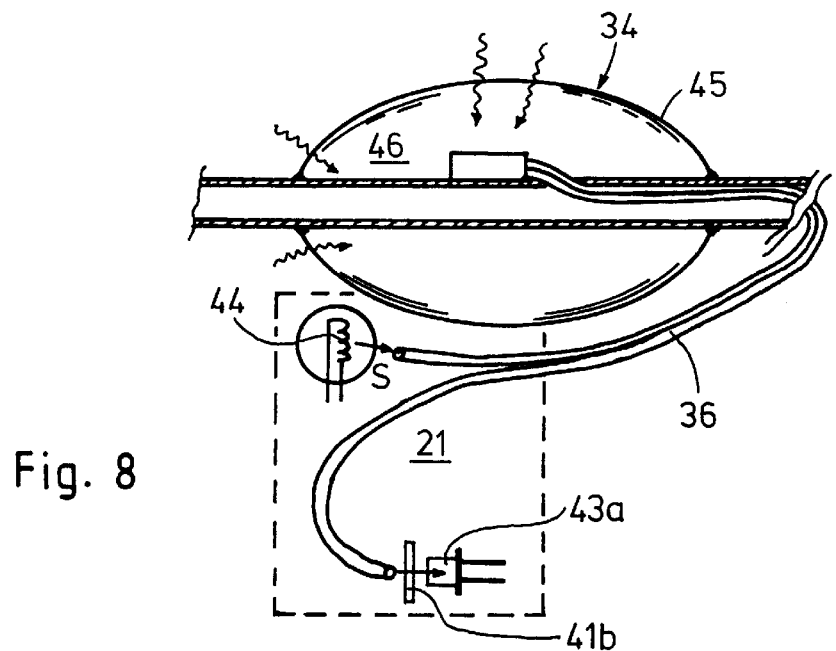
FIG. 8 illustrates more detailed another detector arrangement applicable to FIG. 1 for measuring the concentration of a defined gaseous component in the gas mixture from the internal tract of the patient. In this case shown the data from the gas mixture in the tonometric balloon guided via optical fibers, which is one of the several alternative embodiments for data transfer procedures from said internal tract.
Figure 9:
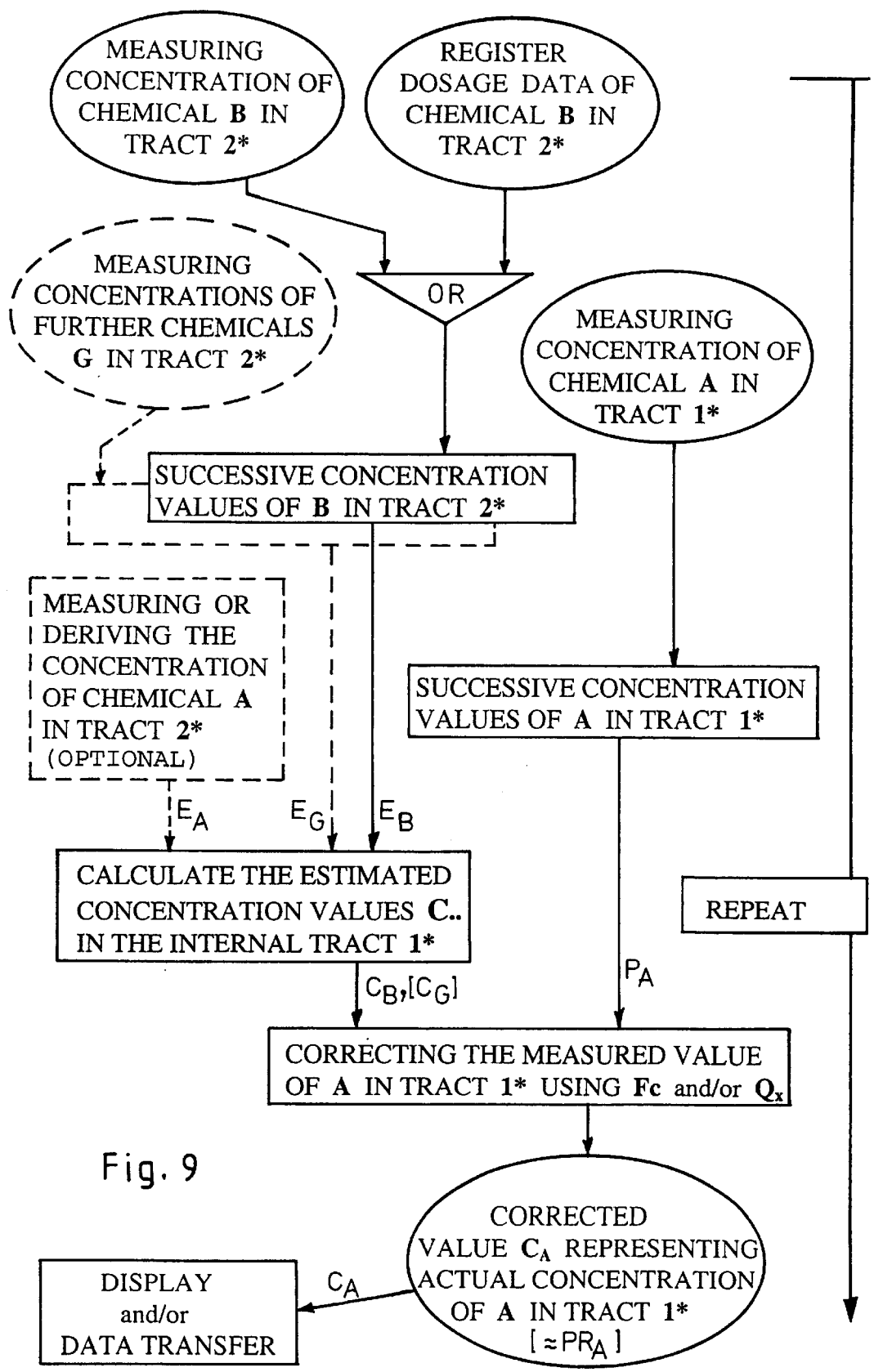
FIG. 9 is a flow chart of the invention illustrating the basic steps thereof.

As earlier said the tonometric measuring of concentration $P_A$ of the first chemical compound A in the first internal tract 1*, like $P_{CO2}$ is an advantageous and preferred alternative. Using the method of invention there is required only one tonometric balloon 31, 34, 35 in the catheter 32, whereupon the sampling part of the tonometric measuring means is small and can be used within different internal tracts 1*, as described earlier. One possible construction of tonometric arrangement is illustrated in FIG. 1. It comprises a tonometric balloon 31 and one or two tubes 32, which connect(s) the sampling chamber 46, formed by the gas-permeable wall 45 of the balloon 31, and a detector unit 21 for measuring e.g. one gas component in the gas mixture within the sampling chamber 46. The balloon and the connecting tube(s) form the tonometric catheter, which is guided into the detection site within the first internal tract, like a hollow organ. The circulation of gas mixture trough the tube 32 can be done to-and-from the sampling chamber in a alternate manner, or trough the tubes 32 as an continues flow as disclosed in the patent publication U.S. Pat. No. 5,479,923. Another possible construction of tonometric arrangement is illustrated in FIG. 8. It comprises a tonometric balloon 34 and for example a pair of optical fibers 36, which connect the sampling chamber 46, formed by the gas-permeable wall 45 of the balloon 31, and a detector unit 21 for measuring e.g. one gas component in the gas mixture within the sampling chamber 46. In this case the gas mixture to be analysed stays in the sampling chamber 46, and the radiation S is sent to the chamber and received therefrom through the optical fiber or a pair of optical fibers 36 by a detecter unit 21. It is also possible use a tonometric balloon 35 of this same type, but provide the sampling chamber with e.g. one or several chemically responsive transistors, which are connected with electrical conductors 37 to a processor unit, not shown in the figures. These two latter examples can be construed and used according to disclosure of the patent publication U.S. Pat. No. 5,186,172.

The wall of the tonometric balloon is usually prepared from dimethyl silicone rubber (35%), the diffusion constants for $CO_2$ and $N_2O$ thereof being in the order of 325 $cm^2/s$ and 435 $cm^2/s$ respectively. Also other polymers can be used for preparing the wall of the tonometric balloon, some examples thereof being cellulose acetate, polycarbonate, polysulfone, different polyethylenes, butyl rubbers etc. These materials have a different diffusion properties for various gas components as compared those for various types of silicone rubbers.

Figure 6:
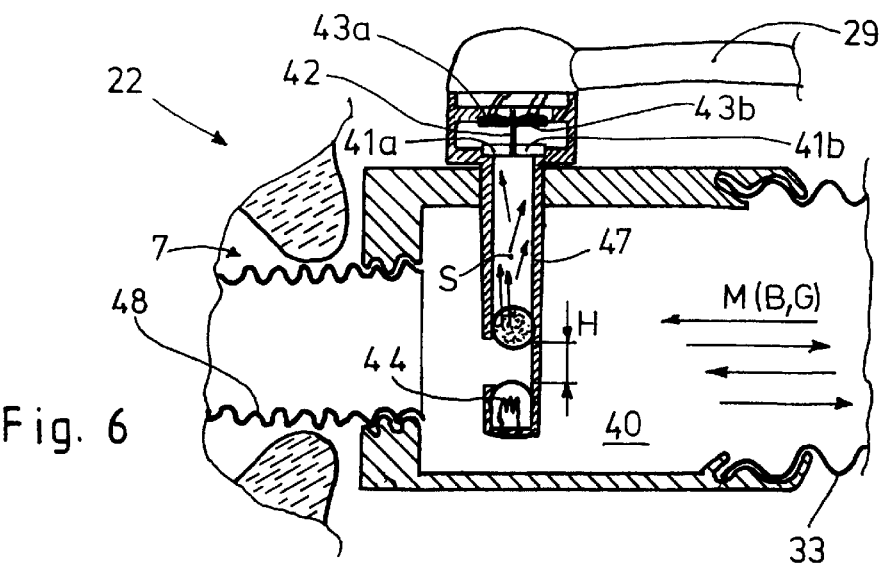
FIG. 6 illustrates more detailed the detector arrangement according to FIG. 1 for measuring the concentrations of defined gaseous components in respiratory air or gas mixture M of the patient. This detector arrangement, which is directly positioned in the intubation tube for the patient's inhalation/exhalation air, is one of the several alternative embodiments for measuring at least the concentration of the chemical compound B dosed.
Figure 7:
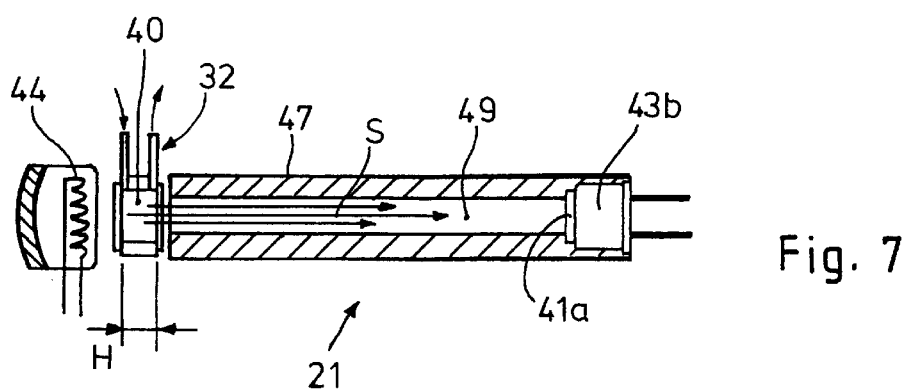
FIG. 7 illustrates more detailed a detector arrangement according to FIG. 1 for measuring the concentration of a defined gaseous component in the gas mixture from the internal tract of the patient. In this case shown the gas mixture is withdrawn from the tonometric balloon via a catheter tubing, which is one of the several alternative embodiments for procedures to provide the measuring of said gas mixture within the tonometric balloon. The detector arrangement shown is also one of the several possible alternative embodiments for measuring the concentration of the chemical compound A in catheter gas mixture.

The detector unit 21, 22 can be any known or new type, which is capable for measuring in the required wavelength area of the radiation S and with required accuracy. At least the initial concentration value $P_A$ or e.g. $P_{CO2}$ of the gaseous first chemical compound is detected using radiation absorption method to have the measurement data, and preferably though not necessarily also the concentration values $E_A$, $E_B$, $R_G$ of the gaseous first, second, third chemical compounds are detected using radiation absorption method to get the measurement data. In FIG. 8 it is schematically illustrated a basic detector unit 21, comprising only the basic parts, which are a radiation source 44, an optical passband filter 41b, and a radiation detector 43a, which provides an electrical signal for further processing. In this embodiment the sampling chamber 46 in the tonometric balloon 34 forms its measuring chamber. In FIG. 7 it is illustrated a detector unit 21, comprising a radiation source 44, a measuring chamber 40 separate from the sampling chamber 46, a hollow radiation tube 47 with an internal guide section 49 for directing the radiation, an optical passband filter 41a, and a radiation detector 43b, which provides an electrical signal for further processing. The measuring cell or chamber 40 also have two connections for tubes 32, which allow flow of the gas mixture from the sampling chamber and trough the measuring chamber. In FIG. 6 it is illustrated a detector unit 21, which is advantageous for analysing the inhaled or exhaled air M of the patient, because it can be installed in the respiration mouth piece provided with a measuring cell or chamber 40 between a dosing/respiration apparatus 26 and the respiratory tract 1 of the patient. This detector unit comprising a radiation source 44, a radiation tube 47, which is either partly hollow or filled with an radiation transparent material, two optical passband filters 41a, 41b, and two radiation detectors 43a, 43b with an separation wall 42 therebetween. Combination of two filters with different transmission bands and two detectors permits measuring of the concentrations of two gas components, but they can be also used for other purposes as known. The detectors provide electrical signals through electrical cable 29 for further processing unit 23. The measuring chamber 40 is connected to an intubation tube 48 on the one side and with a connection tube 33 to the dosing/respiration apparatus 26. All of these measuring chambers are provided with an analysis cell with permanent absorption length(s) H, which is a general practise. Of course also other types of detector units can be employed. The different detector units and their functions are generally known, so that they not described more in detail.

In cases the second chemical compound B, like nitrous oxide and other anaesthetic gasses or liquids, are being dosed into the patient directly from a dosing apparatus 26 its is not necessary to measure by detection, as described in the preceding chapter, in a conventional manner, but the required concentration values $E_B$ of the second chemical compound B are derived or transmitted from the dosage D data already present in the dosing apparatus 26.

In general form according to the invention at least one of the initial concentration values $P_A$ and/or $E_A$ and/or $E_B$ and/or $R_G$ etc. of the gaseous first and/or second and/or third chemical compounds A, B, G are detected by radiation absorption in a measuring chamber(s) 40 or from a sampling chamber 46, which are/is in connection with the respective one of said tracts 1–8. Said radiation is electromagnetic radiation S provided to function with specific wavelength bands λp each of which is arranged in a predetermined manner within an area of an absorption peak λb of said gaseous first chemical compound A, e.g. $CO_2$ as described, and optionally within an area of an absorption peak of said gaseous second chemical compound B, e.g. $N_2O$ as described, and/or third chemical compound G, e.g. some other anaesthetic gas as described, respectively. Specifically concentration values $P_{CO2}$ of carbon dioxide and concentration values $P_{N2O}$ of nitrous oxide from the internal tract 1* are detected using two wavelength bands $\lambda b_1$, $\lambda b_2$ respectively in the infrared area of said radiation S. Finally each of said successive and corrected concentration value $C_{CO2}[n]$ is displayed or transmitted to further data processing as final compensated concentration values in a monitoring equipment 25.

As a summary, according to the invention the measured concentration values of at least a first chemical compound A within a first internal tract 1* of a patient, which concentration values $P_A$ in initial measured state are affected by a second chemical compound B, are compensated in conditions, where the second chemical compound is becoming present in the body of said patient and render these initial measured concentration values $P_A$ to deviate from actual concentration values $PR_A$, if some degree of compensation is not applied. The second chemical compound B has in practise a limited transfer speed to mix with the first chemical compound at least in a detection site for said measured concentration values $P_A$, within said first internal tract 1. Concentration values $E_B$ of at least said second chemical compound B in a second tract 2* of said patient is measured or respective data D derived several times during a time period T including first chemical compound measurements in said first internal tract 1* or from the beginning of presence for absorption and/or diffusion to the patient, person or animal. Estimated concentration values $C_B$ of said second chemical compound is determined simulating its non-detected concentrations in said first internal tract 1*. The measured/detected initial concentration values $P_A$ of said first chemical compound A in the first internal tract 1* are corrected by a compensating factor Fc and optionally Fc* and/or $Fc_1$ and or $Fc_2$ etc. Each said successive and corrected concentration value $C_A$ is made evident as the respective one of the compensated concentration values.

What is claimed is:

1. Method for compensating measured concentration values of at least a first chemical compound (A) within a first internal tract (1*) of a patient, which concentration values ($P_A$) as measured are affected by a second chemical compound (B), which is becoming present in the body of said patient and has a limited transfer speed to mix with the first chemical compound at least in a detection site for said measured concentration values ($P_A$), rendering these measured concentration values ($P_A$) to deviate from actual concentration values ($PR_A$) within said first internal tract (1*), characterised in that concentration values ($E_B$) of at least said second chemical compound (B) in a second tract (2*) of said patient is measured or derived several times during a time period (T) including first chemical compound measurements in said first internal tract (1*); that estimated concentration values ($C_B$) of said second chemical compound are determined simulating its non-detected concentrations in said first internal tract of the patient; that by detection in the first internal tract (1*) measured initial concentration values ($P_A$) of said first chemical compound (A) are corrected by at least a compensating factor (Fc or Qx); and that each said successive and corrected concentration value ($C_A$) is the respective one of the compensated concentration values.

2. Method according to claim 1, characterised in that additionally the concentration value ($E_A$) of said first chemical compound (A) in the second tract (2*) of said patient is measured or derived several times during said time period (T) including first chemical compound measurements in said first internal tract (1*); and that said time period (T) includes first traces of said second chemical compound (B) within or in contact with said patient.

3. Method according to claim 1, characterised in that:
said compensating factor (Fc) is a first predetermined function (II) of at least one said estimated concentration value ($C_B[n]$) of said second chemical compound in said first internal tract (1*), and said compensating factor (Fc) is a product of an empirical constant (K) and at least said estimated concentration value ($C_B[n]$); or said compensating factor (Qx) is an empirical variable or constant (Q1), and the measured initial concentration values ($P_A$) of said first chemical compound (A) are further corrected by term(s), which is/are a function of empirical variable or constant (Q2, Q3) and estimated concentration values ($C_B$, $C_G$), where said variables or constants are depending on the absorptivities of said chemical components within the first tract 1*.

4. Method according to claim 3, characterised in that said estimated concentration value ($C_B[n]$) of said second chemical compound (B) is a cumulative function (III) of the previous, during said time period (T) measured or derived concentration values ($E_B[0 \ldots n]$) from the second tract (2*) providing said simulation for said estimated concentration value.

5. Method according to claim 3, characterised in that said estimated concentration value(s) ($C_B[n]$) of said second chemical compound (B) is a cumulative function (III) of its previous measured or derived concentration value(s) ($E_B[0 \ldots n]$) and at least one in succession previous estimated concentration value ($C_B[n-1]$); and that this estimated concentration value(s) ($C_B[n]$) of said second chemical compound (B) is directly related to both a measured or derived concentration value ($E_B[n]$) and a previous estimated concentration value ($C_B[n-1]$) thereof, and is additionally related to a constant or variable parameter ($\gamma$).

6. Method according to claim 5, characterised in that said constant or variable parameter ($\gamma$) is either a constant (IVe) or inversely related (IVa . . . IVd) to at least to a corrected concentration value ($C_A[n-1]$) of said first chemical compound (A) in the first internal tract (1*) and optionally to a measured concentration value ($E_A[n-1]$) of said first chemical compound (A) in the second tract (2*).

7. Method according to claim 1, characterised in that said first chemical compound (A) is arranged to be in a gaseous state for detection of its measured initial concentration ($P_A$) in the first internal tract (1*) and in a gaseous state for detection or deriving of its measured concentration ($E_A$) in the second tract (2*); and that said second chemical compound (B) having a variable concentration with time as mixing with said first chemical compound in the first internal tract (1*) is also arranged to be in a gaseous state for detection of its actual concentration ($E_B$) in the second tract (2*).

8. Method according to claim 1, characterised in that at least said first internal tract comprises an accessible internal organ of the body of the patient; that the second tract is an internal tract or comprises an internal or external organ of the body of the patient; and that the said first chemical compound (A) is carbon dioxide ($CO_2$) and said second chemical compound (B) is nitrous oxide ($N_2O$) or some other anaesthetic gas.

9. Method according to claim 8, characterised in that said first chemical compound (A) is arranged to be in the gaseous state using tonometric means (31, 34, 35) within said first internal tract (1*); and that said second chemical compound (B) and said first chemical compound (A) is arranged to be in the gaseous state using air or gas mixture provided to or from said second internal tract (2*).

10. Method according to claim 8, characterised in that said first internal tract (1*) is an intestinal tract (1), or a respiratory tract (2), or an urinary tract (3), or one of the vascular tracts (4), or a genital tract (5); and said second tract (2*) is an intestinal (1) tract, or a respiratory tract (2), or an urinary tract (3), or a nervous tract (8), or one of the vascular tracts (4), or a genital tract (5), other than the first internal tract, or a cutaneous or mucous area (6, resp. 7) of the body of the patient.

11. Method according to claim 1, characterised in that said first chemical compound (A) is arranged to be in the gaseous state using tonometric means (31, 34, 35) within said first internal tract (1*); and that said second chemical compound (B) and said first chemical compound (A) are arranged to be in the gaseous state using air or gas mixture provided to or from said second internal tract (2*).

12. Method according to claim 1, characterised in that said first internal tract (1*) is an intestinal tract (1), or a respirator tract (2), or an urinary tract (3), or one of the vascular tracts (4), or a genital tract (5); and said second tract (2*) is an intestinal (1) tract, or a respiratory tract (2), or a urinary tract (3), or a nervous tract (8), or one of the vascular tracts (4), or a genital tract (5), other than the first internal tract, or a cutaneous or mucous area (6, resp. 70) of the body of the patient.

13. Method according to claim 1, characterised in that further a concentration values ($R_G$) of a third or several chemical compound(s) (G), which is/are transferring to the detection site for said measured concentration values ($P_A$) of the first chemical compound (A) within said first internal tract (1*), is/are measured or derived in an third tract (3*) deviating from the first internal tract, and concentration value(s) ($C_G$) thereof islare estimated without detection within said first internal tract, and said initial concentration values ($P_A$) of said first chemical compound (A) is corrected by an additional compensation factor (Fc* or $Fc_X$), which is a second predetermined function ($I_{BG}$, $I_G$) of said estimated concentration values ($C_G[n]$) of at least said third chemical compound in said first internal tract (1*).

14. Method according to claim 1, characterised in that:
{I} the initial concentration value ($P_A$) of the gaseous first chemical compound and/or the concentration values ($E_A$, $E_B$, $E_G$) of the gaseous first, second, third chemical compounds are detected for measurement by radiation absorption method; or {II} the concentration values ($E_B$) of the second and/or the third chemical compound (B, G) are derived from the dosage (D) data in dosing apparatus (26).

15. Method according to claim 13, characterised in that at least one of said initial concentration values ($P_A$, $E_A$, $E_B$, $E_G$ etc.) of the gaseous first and/or second and/or third chemical compounds (A, B, G) are detected by radiation absorption in an analysis cell(s) (40) with permanent absorption length(s) (H) and in connection with the respective one of said tracts (1–7); and that said radiation (S) is electromagnetic radiation provided to function with specific wavelength bands ($\lambda b$) each of which is arranged in a predetermined manner within an area of an absorption peak ($\lambda p$) of said gaseous first chemical compound (A) and optionally within an area of an absorption peak of said gaseous second chemical compound (B) and/or third chemical compound (G) respectively.

16. Method according to claim 1, characterised in that said estimated concentration value ($C_B[n]$) is calculated using a recursive exponential smoothing, known per se, with a measured or derived concentration value ($E_B[n]$) of the second chemical compound (B) from said second internal tract (2*) successive to prevailing estimated concentration value ($C_B[n-1]$), and with a variable smoothing parameter ($\gamma$), which has at least successive actual concentration values of the first chemical compound (A) from said first and/or second internal tract (1* and/or 2*) as variables, and said estimated concentration value is an inverse function of these actual concentration values of the first chemical compound from said first and second internal tract.

17. A method for compensating measured concentration values of carbon dioxide ($CO_2$) within a gastrointestinal tract (1) of a patient, which concentration values are affected by at least nitrous oxide ($N_2O$), which is being dosed into the respiratory gas (M) of said patient and has a limited absorption and/or diffusion and/or transport speed to a detection site of said carbon dioxide concentration measurement, rendering its measured concentration values ($P_{CO2}$) to deviate from actual concentration values, characterised in that concentration values ($E_{N2O}$) of at least nitrous oxide are measured or derived several times in the inhaled or exhaled gas (M) of said patient during a period (T) of a clinical operation; that concentration values ($C_{N2O}$) for nitrous oxide within the gastrointestinal tract are estimated without detection; that the measured initial concentration values ($P_{CO2}[n]$) of carbon dioxide in the gastrointestinal tract are corrected by a compensating factor (Fc); and that each said successive and corrected concentration value ($C_{CO2}[n]$) is displayed as final compensated concentration values.

18. The method according to claim 17, characterised in that additionally a concentration value ($E_{CO2}$) of carbon dioxide is measured or derived several times in the inhaled or exhaled gas (M) of said patient during a period (T) of the clinical operation; that said compensating factor (Fc) is a predetermined function (II) of an empirical constant (K) and at least one said estimated concentration value ($C_{N2O}$); and that said estimated concentration value ($C_{N2O}$) is a predetermined cumulative function (III) of a prevailing concentration value ($E_{N2O}$) in the respiratory tract (2) and previous estimated concentration values ($C_{N2O}[n-1]$) in the gastrointestinal tract (1) during dosage time (T) of nitrous oxide ($N_2O$) into a patient under said clinical operation.

19. The method according to claim 17, characterised in that additionally concentration values ($E_G$) of one or several of those other anaesthetic gases, which is/are being dosed into the respiratory air of said patient, is/are measured or derived several times in the inhaled or exhaled gas (M) of said patient during a period (T) of a clinical operation; that concentration values ($C_G$) for specified anaesthetic gas component(s) within gastrointestinal tract (1) are estimated without detection; and that said compensating factor (Fc) is formulated to provide a further correction for measured initial concentration values ($P_{CO2}[n]$) of carbon dioxide.

20. The method according to claim 17, characterised in that said concentration values ($C_{N2O}$) for nitrous oxide are measured or derived, by detection or by using dosing data (D) respectively, from that area or channel forming a dosing route of the nitrous oxide ($N_2O$) into the patient.

21. The method according to claim 17, characterised in that said concentration values ($E_{CO2}$, $E_{N2O}$) of carbon dioxide and nitrous oxide from a respiratory tract (2) are detected using two wavelength bands ($\lambda b_1$, $\lambda b_2$) in the infrared area of radiation.

22. The method according to claim 17, characterised in that method is utilised during surgical operations to detect the rate of metabolism and/or perfusion in the patient.

* * * * *